United States Patent
Ovchinnikov

(10) Patent No.: US 12,364,623 B2
(45) Date of Patent: Jul. 22, 2025

(54) EFFICIENT LASERS FOR TISSUE DISRUPTION

(71) Applicant: Alcon Inc., Fribourg (CH)

(72) Inventor: Mikhail Ovchinnikov, Dana Point, CA (US)

(73) Assignee: Alcon Inc., Fribourg (CH)

( * ) Notice: Subject to any disclaimer, the term of this patent is extended or adjusted under 35 U.S.C. 154(b) by 338 days.

(21) Appl. No.: 17/937,859

(22) Filed: Oct. 4, 2022

(65) Prior Publication Data
US 2023/0113339 A1   Apr. 13, 2023

Related U.S. Application Data

(60) Provisional application No. 63/253,601, filed on Oct. 8, 2021.

(51) Int. Cl.
*A61F 9/008* (2006.01)

(52) U.S. Cl.
CPC ............... *A61F 9/00825* (2013.01); *A61F 2009/00887* (2013.01)

(58) Field of Classification Search
None
See application file for complete search history.

(56) References Cited

U.S. PATENT DOCUMENTS

| | | | |
|---|---|---|---|
| 5,225,884 A | 7/1993 | Stark et al. | |
| 5,738,677 A * | 4/1998 | Colvard | G02B 6/241 606/4 |
| 6,055,259 A | 4/2000 | Frey et al. | |
| 6,067,311 A | 5/2000 | Morton et al. | |
| 6,080,148 A | 6/2000 | Damasco | |
| 6,156,030 A | 12/2000 | Neev | |
| 6,258,082 B1 * | 7/2001 | Lin | A61F 9/00804 606/4 |
| 7,479,138 B2 | 1/2009 | Hindi et al. | |
| 7,630,418 B2 | 12/2009 | Franjic et al. | |

(Continued)

FOREIGN PATENT DOCUMENTS

| DE | 3333575 C2 | 9/1992 |
|---|---|---|
| KR | 20130109664 A | 10/2013 |

(Continued)

OTHER PUBLICATIONS

Anonymous: "Kuhnke Laser Shutter DS200x8", Kendrions—Technical information, Feb. 21, 2017, XP002806981. Retrieved from the Internet: URL: https://www.kendrion.com/fileadmin/user_upload/Downloads/Brochures_and_Flyers/Electromagnets_Actuators/brochure-lasershutter-ds200x8-kendrion-kuhnke.pdf [retrieved on Jul. 1, 2022].

(Continued)

*Primary Examiner* — Mallika D Fairchild

(57) ABSTRACT

Methods are disclosed for operating a laser. Such methods may comprise operating the laser to emit electromagnetic energy in an infrared range in pulses with a pulse duration of greater than 1 ns. The wavelength of infrared electromagnetic energy may be in a range of about 2.6μ to about 3.3μ or about 1.8μ to about 2.1μ. The pulses may have a pulse energy selected to deliver an energy density of 2,500 J/cm$^3$ or greater. The laser electromagnetic energy may be delivered for a medical application, such as cataract surgery to break apart a cataractous lens by photodisruption.

7 Claims, 3 Drawing Sheets

(56) References Cited

U.S. PATENT DOCUMENTS

| | | |
|---|---|---|
| 7,696,466 B2 | 4/2010 | Rizoiu et al. |
| 8,025,659 B2 | 9/2011 | Bischoff et al. |
| 8,029,501 B2 | 10/2011 | Miller |
| 8,279,901 B2 | 10/2012 | Karavitis |
| 8,506,559 B2 | 8/2013 | Raksi |
| 8,518,030 B2 | 8/2013 | Holliday |
| 8,652,122 B2 | 2/2014 | Bischoff et al. |
| 8,920,407 B2 | 12/2014 | Raksi et al. |
| 9,044,303 B2 | 6/2015 | Kurtz et al. |
| 9,054,479 B2 | 6/2015 | Karavitis |
| 9,660,412 B2 | 5/2017 | Vogler et al. |
| 9,724,235 B2 | 8/2017 | Vogler et al. |
| 9,755,393 B2 | 9/2017 | Vogler et al. |
| 9,931,447 B2 | 4/2018 | Layser |
| 10,512,586 B1 | 12/2019 | Lee |
| 10,624,786 B2 | 4/2020 | Wysopal et al. |
| 10,702,338 B2 | 7/2020 | Shazly et al. |
| 10,881,551 B2 | 1/2021 | Kraemer et al. |
| 10,925,769 B2 | 2/2021 | Kraemer |
| 11,197,781 B2 | 12/2021 | Wittnebel |
| 2009/0213330 A1 | 8/2009 | Silverstein et al. |
| 2014/0276676 A1 | 9/2014 | Schuele et al. |
| 2017/0246036 A1* | 8/2017 | Kraemer ............ A61F 9/00736 |
| 2018/0360657 A1 | 12/2018 | Bor et al. |
| 2019/0201238 A1 | 7/2019 | Bacher et al. |
| 2021/0135424 A1 | 5/2021 | Bacher et al. |
| 2021/0137739 A1 | 5/2021 | Kraemer |
| 2022/0354575 A1 | 11/2022 | Jung et al. |
| 2023/0116921 A1 | 4/2023 | Jung et al. |
| 2023/0178953 A1 | 6/2023 | Karim et al. |

FOREIGN PATENT DOCUMENTS

| | | |
|---|---|---|
| RU | 2349998 C2 | 3/2009 |
| WO | 2009108543 A2 | 9/2009 |

OTHER PUBLICATIONS

Peter Gregorčič, Matija Jezeršek, and Janez Možina, Optodynamic energy-conversion efficiency during an Er:YAG-laser-pulse delivery into a liquid through different fiber-tip geometries, Journal of Biomedical Optics 17(7), 075006 (Jul. 2012)).

Wikipedia. "Optical Chopper." Retrieved from https://en.wikipedia.org/w/index.php?title=Optical_chopper&oldid=943497792 on May 12, 2020.

* cited by examiner

EFFICIENT LASERS FOR TISSUE DISRUPTION

PRIORITY CLAIM

This application claims the benefit of priority of U.S. Provisional Patent Application Ser. No. 63/253,601 titled "EFFICIENT LASERS FOR TISSUE DISRUPTION," filed on Oct. 8, 2021, whose inventor is Mikhail Ovchinnikov, which is hereby incorporated by reference in its entirety as though fully and completely set forth herein.

TECHNICAL FIELD

The present disclosure is directed to lasers for tissue disruption.

BACKGROUND

Lasers are used in many different medical procedures including a number of different ophthalmic procedures. For example, lasers may be used in cataract surgery, such as for fragmenting the cataractous lens. In some procedures, a laser is used for initial fragmentation of the lens, followed by phacoemulsification of the lens by an ultrasonic handpiece to complete the breakdown of the lens for removal. In other procedures, the laser may be used for complete fragmentation or phacoemulsification of the lens for removal, without the need for a separate application of ultrasonic energy. Lasers may also be used for other steps in cataract surgery, such as for making the corneal incision(s) and/or opening the capsule.

Lasers may also be used in vitreoretinal surgery. In some procedures, a laser may be used for vitrectomy, to sever or break the vitreous fibers for removal. The laser may be incorporated into a vitrectomy probe, and the energy from the laser may be applied to the vitreous fibers to sever or break the vitreous fibers for removal.

In other vitreoretinal applications, lasers may be used for photocoagulation of retinal tissue. Laser photocoagulation may be used to treat issues such as retinal tears and/or the effects of diabetic retinopathy.

U.S. Patent Application Publication No. 2018/0360657 discloses examples of an ophthalmic laser system. That application describes laser uses such as for forming surgical cuts or for photodisrupting ophthalmic tissue as well as for cataract surgery, such as laser-assisted cataract surgery (LACS). U.S. Patent Application Publication No. 2019/0201238 discloses other examples of an ophthalmic laser system. That application describes laser uses such as in a vitrectomy probe for severing or breaking vitreous fibers. U.S. Patent Application Publication No. 2018/0360657 and U.S. Patent Application Publication No. 2019/0201238 are expressly incorporated by reference herein in their entirety.

U.S. Pat. No. 8,029,501 discloses laser cutting by impulsive heat deposition. U.S. Pat. No. 8,029,501 is expressly incorporated by reference herein in its entirety.

SUMMARY

The present disclosure is directed to methods of operating lasers. The lasers may be operated for photodisruption.

In certain embodiments, a method of operating a laser comprises operating the laser to emit electromagnetic energy in an infrared range, wherein the wavelength of infrared electromagnetic energy is in a range of about 2.6 microns (2.6μ) to about 3.3 microns (3.3μ) or about 1.8 microns (1.80 to about 2.1 microns (2.1μ); and operating the laser in pulses, wherein the pulses have a pulse duration of greater than 1 nanosecond (1 ns). The pulses may have a pulse duration of 2 nanoseconds (2 ns) or greater.

In certain embodiments, the pulses have a pulse energy selected to deliver an energy density of 2,500 joules per cubic centimeter (2,500 J/cm$^3$) or greater. In other embodiments, the pulses have a pulse energy selected to deliver an energy density of 5,000 joules per cubic centimeter (5,000 J/cm$^3$) or greater. In other embodiments, the pulses have a pulse energy selected to deliver an energy density of 10,000 joules per cubic centimeter (10,000 J/cm$^3$) or greater.

In certain embodiments, the wavelength of infrared electromagnetic energy is in a range of about 2.6 microns (2.6μ) to about 3.3 microns (3.3μ). In such embodiments, the laser may be operated to deliver a pulse energy of 150 microjoules (1500) or greater.

In certain embodiments, the wavelength of infrared electromagnetic energy is in a range of about 1.8 microns (1.8μ) to about 2.1 microns (2.1μ). In such embodiments, the laser may be operated to deliver a pulse energy of about 4 millijoules (4 mJ) or greater.

In certain embodiments, the laser electromagnetic energy may be delivered from an optical fiber having a tip area of about 300 square microns (300μ$^2$) to about 0.5 square millimeters (0.5 mm$^2$).

In certain embodiments, the laser electromagnetic energy is delivered for a medical application. For example, the laser electromagnetic energy may be delivered for cataract surgery. The laser electromagnetic energy may be directed at a cataractous lens. The mechanism of action of breaking up the cataractous lens may be photodisruption. The laser energy may be absorbed by a small volume of water that is adjacent to a laser optical fiber tip.

In other embodiments, a method of operating a laser comprises operating the laser to emit electromagnetic energy in an infrared range, wherein the wavelength of infrared electromagnetic energy is in a range of about 2.6μ to about 3.3μ or about 1.8μ to about 2.1μ; and operating the laser in pulses, wherein the pulses have a pulse energy selected to deliver an energy density of 2,500 J/cm$^3$ or greater. The pulses may have a pulse energy selected to deliver an energy density of 5,000 J/cm$^3$ or greater. The pulses may have a pulse energy selected to deliver an energy density of 10,000 J/cm$^3$ or greater.

In other embodiments, a method of operating a laser comprises directing a laser fiber tip adjacent to a cataractous lens; operating the laser to emit electromagnetic energy in an infrared range, wherein the wavelength of infrared electromagnetic energy is in a range of about 2.6μ to about 3.3μ or about 1.8μ to about 2.1μ; and operating the laser in pulses, wherein the pulses have a pulse duration of greater than 1 ns.

In certain embodiments, the pulses may have a pulse duration of 2 ns or greater. In other embodiments, the pulses may have a pulse duration of 5 ns or greater. In other embodiments, the pulses may have a pulse duration of 10 ns or greater.

Further examples and features of embodiments of the invention will be evident from the drawings and detailed description.

BRIEF DESCRIPTION OF THE DRAWINGS

The accompanying drawings, together with the description, serve to explain the principles of the present disclosure.

Figure 1:
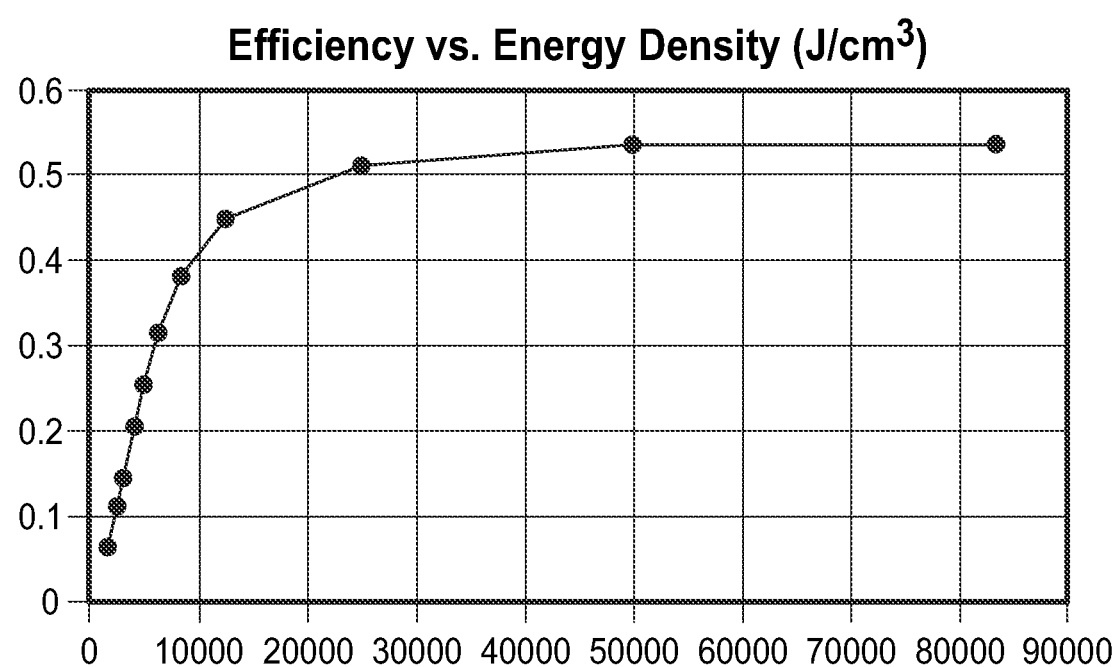
FIG. 1 shows a relationship between laser efficiency and pulse energy density.

The accompanying drawings may be better understood by reference to the following detailed description.

DETAILED DESCRIPTION

For the purposes of promoting an understanding of the principles of the disclosure, certain examples will be described. It will nevertheless be understood that no limitation of the scope of the claims is intended by the examples described herein. Any alterations and further modifications to the illustrated or described systems, devices, instruments, or methods, and any further application of the principles of the present disclosure, are fully contemplated as would normally occur to one skilled in the art to which the disclosure relates. In particular, the features, components, and/or steps described with respect to one implementation of the disclosure may be combined with features, components, and/or steps described with respect to other implementations of the disclosure.

Laser interaction with tissue generally can be classified as one of two types: (1) photocoagulation, referring to the effect of heat on the tissue (or simply burning), and (2) photodisruption, referring to the effect of tissue expansion due to pressure created by the laser. The action of certain lasers as described in U.S. Pat. No. 8,029,501, referenced above, can be characterized as photodisruption. This disclosure is directed to lasers whose action is, or primarily is, photodisruption.

A goal in photodisruption is to maximize the disruption effect while keeping the amount of deposited heat to a minimum. The disruption is produced by the following mechanism. A fast laser pulse is absorbed by a small volume of water that is adjacent to the tip of the laser fiber. Since the pulse is faster than it takes for water to expand, the small volume of water becomes highly pressurized. The expansion of this volume into vapor pushes the adjacent tissue apart and mechanically breaks it.

U.S. Pat. No. 8,029,501 discloses lasers operating in the infrared range wherein the laser pulse duration is shorter than the time it takes sound (or a pressure wave) to travel through the heated layer. That patent states that its invention is directed to the use of a "short IR [infrared] pulse," which the patent defines as a pulse duration from 1 ps to 1 ns. (U.S. Pat. No. 8,029,50, col. 8, lines 52-59.) That patent states that "the concepts embodied in this patent are to use <1 ns pulses." (U.S. Pat. No. 8,029,50, col. 14, lines 60-65.) That patent further states, "The pulse duration in this case should be less than 1 ns and ideally should be between 1 to 100 ps." (U.S. Pat. No. 8,029,50, col. 16, lines 53-55.)

Through modeling and experimentation, the inventor has invented methods of operating lasers that significantly improve the efficiency of the lasers over that of existing lasers. Moreover, the inventor has invented methods of operating lasers efficiently outside the limitations previously believed to be required by persons of ordinary skill in the art. Such methods include operating conditions with a broad range of pulse durations and pulse energies.

The efficiency of disruption can be defined as the ratio of energy of mechanical disruption to the total energy of the laser pulse. The energy of mechanical disruption can be measured by observing the resulting vapor bubble when operating in water. The energy of the bubble can be expressed as $E=P*V_{max}$, where P is the atmospheric pressure and $V_{max}$ is the maximum volume of the bubble produced by the laser pulse.

Experimentally, using the inventive methods as described herein, and under varying conditions in accordance with the disclosure, disruption efficiency has been measured in the range of about 0.1 to about 0.35, depending on conditions of the laser pulse. The efficiency of previous infrared lasers used for contact cutting (at the fiber tip) has been significantly lower. Reference 1 (Peter Gregorčič, Matija Jezeršek, and Janez Možina, *Optodynamic energy-conversion efficiency during an Er: YAG-laser-pulse delivery into a liquid through different fiber-tip geometries*, Journal of Biomedical Optics 17(7), 075006 (July 2012)) reports the best efficiency of 0.03. For the non-contact type (ultrafast, typically femtosecond, laser that is non-linearly absorbed at the focal point of the beam) the efficiency is known to be close to 0.1.

For a given laser wavelength, efficiency is a function of two main variables: (1) pulse energy density (pulse energy per volume of heated water), and (2) pulse duration. Through modeling, the inventor has determined the following dependences.

Dependence of efficiency on the energy density: FIG. 1 shows what the inventor has determined to be a relationship between laser efficiency and the pulse energy density, where the pulse energy density is the pulse energy divided by a volume of water being heated. In the case of a flat fiber surface, this volume is given by the product of the cross-sectional area of the fiber tip and the penetration depth. In one example, a laser emits electromagnetic energy at a wavelength of 2.9μ (microns), which yields a penetration depth of about 0.8 In another example, a laser emits electromagnetic energy at a wavelength of 2.775μ (microns), which yields a penetration depth of about 2 FIG. 1 shows an example of a laser emitting electromagnetic energy at a wavelength of 2.9μ with a pulse duration of 1 ns. As can be seen in FIG. 1, low energy densities result in low efficiency, and most known lasers operate in this range. At energy densities at about 2,500 $J/cm^3$ and above, the laser efficiency is suitable for certain applications. At energy densities at about 5,000 $J/cm^3$ and above, the laser efficiency is significantly greater than that achieved with known prior lasers. At energy densities at about 10,000 $J/cm^3$ and above, the laser efficiency begins to approach maximum efficiency.

Figure 2:
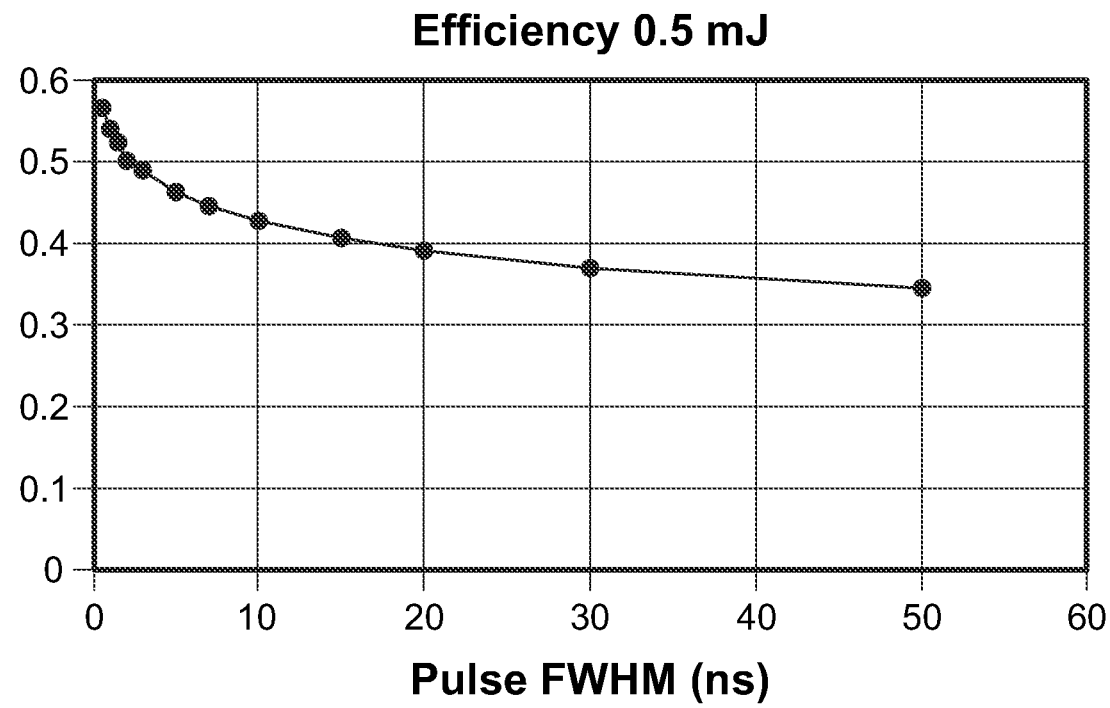
FIG. 2 shows a relationship between laser efficiency and pulse duration at a pulse energy of 0.5 mJ.
Figure 3:
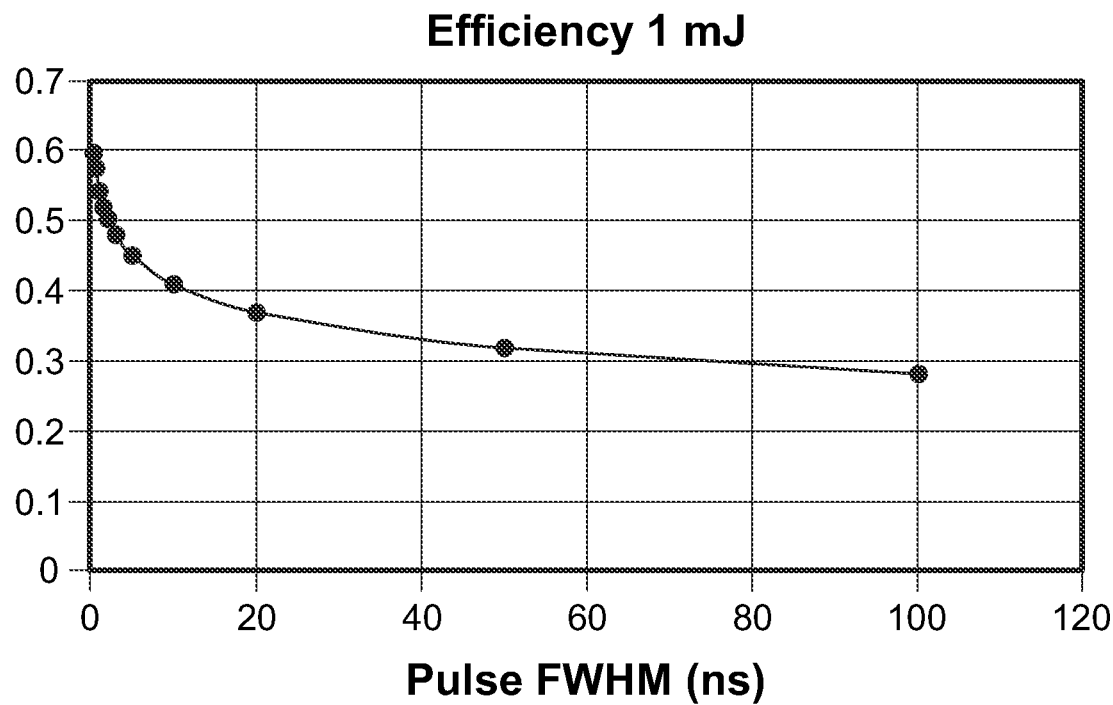
FIG. 3 shows a relationship between laser efficiency and pulse duration at a pulse energy of 1 mJ.
Figure 4:
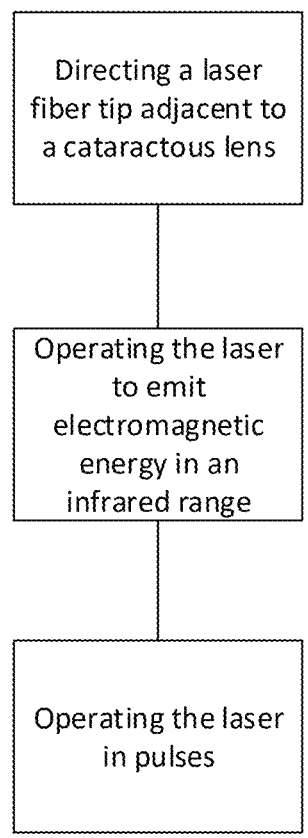
FIG. 4 shows a method of operating a laser.

Dependence of efficiency on the pulse duration: FIGS. 2 and 3 show what the inventor has determined to be a relationship between laser efficiency and the pulse duration, where the pulse duration (the x-axis) in FIGS. 2 and 3 is in nanoseconds (pulse duration being full width at half maximum (FWHM)). The example of FIG. 2 is for a laser yielding a penetration depth of 1μ and having a pulse energy of 0.5 mJ. The example of FIG. 3 is for a laser yielding a penetration depth of 1μ and having a pulse energy of 1 mJ. As can be seen in FIGS. 2 and 3, while efficiency is high at pulse durations less than 1 ns, there is not a significant loss of efficiency at higher pulse durations. Pulse durations of 1 ns and above still yield high efficiencies.

Through modeling and experimentation, the inventor has invented methods of operating lasers with high efficiency. In a modeling scenario, for a laser operating in the infrared range at pulse durations on a picosecond/nanosecond scale, the inventor has determined the efficiency of a laser as a function of pulse duration, penetration depth, and pulse energy.

For certain applications, e.g., medical applications such as cataract surgery in which the laser electromagnetic energy is directed at a cataractous lens, the mechanism of action is photodisruption. In cataract surgery, the user (e.g., physician) directs the laser energy at the cataractous lens to break up the lens. The laser energy is absorbed by a small volume of water that is adjacent to the tip of the laser fiber. The small volume of water becomes highly pressurized and expands, pushing the adjacent tissue apart and mechanically breaking it.

In applications in which the laser energy is absorbed by a small volume of water that is adjacent to the tip of the laser fiber, the penetration depth is a function of the wavelength of the electromagnetic energy emitted by the laser. In one example, a laser operating in a wavelength range of about 2.6μ to about 3.3μ may be used. A laser operating at a wavelength of, e.g., 2.775μ results in a penetration depth of about 2. A laser operating at a wavelength of, e.g., 2.9μ results in a penetration depth of about 0.8 As another example, a laser operating in a wavelength range of about 1.8μ to 2.1μ may be used. A laser operating at a wavelength of, e.g., 1.93μ, results in a penetration depth of about 76μ.

In an experimental set-up, with a laser emitting electromagnetic energy at a wavelength of about 2.7μ to 2.8μ, or about 2.775μ, operating at a pulse duration on a picosecond/nanosecond scale, efficiencies were measured in the range of about 0.1 to about 0.35. The example laser used was a chromium-doped zinc selenide laser (available from IPG Photonics).

With reference again to FIG. 1, the dependence of laser efficiency on energy density can be seen. Most lasers operate in a narrow range on the left-most side of the graph in FIG. 1, with very low energy densities and very low efficiencies. The inventor has invented methods of operating lasers beyond the conventional parameters, yielding significantly higher efficiencies than previously obtained. In accordance with the present disclosure, operating a laser at energy densities of 2,500 J/cm$^3$ and above yields efficiencies suitable for certain applications. In accordance with the present disclosure, operating a laser at energy densities of 5,000 J/cm$^3$ and above yields high efficiencies. In accordance with the present disclosure, operating a laser at energy densities of 10,000 J/cm$^3$ and above approaches maximum efficiency.

The energy density is a function of the pulse energy from the laser and the volume of heated water. The volume of heated water is a function of the penetration depth (which is a function of wavelength as described above) and the geometry of the laser optical fiber tip (e.g., the area from which the laser electromagnetic energy is emitted).

In one example, the fiber tip is circular and has a diameter in a range of about 20μ to about 0.8 mm. This corresponds to a fiber area of about 300μ$^2$ to about 0.5 mm$^2$. For example, the fiber tip may be circular and may have a diameter of about 100μ or about 200 The fiber may be made of any suitable material, for example sapphire.

The pulse energy has to be substantially greater than the threshold energy of the heated volume, defined by the water equation of state. The volume, as mentioned above, is a function of the penetration depth (a function of wavelength) and the fiber tip geometry. Depending on the laser operating wavelength and resulting penetration depth, and also depending on the geometry of the fiber tip, a range of laser energies can be employed. For example, pulse energy may be in a range of about 100 to about 100 mJ. For a given fiber tip geometry, for smaller penetration depths, less pulse energy is needed to achieve the desired energy density and resulting efficiency. For larger penetration depths, higher pulse energy is needed to achieve the desired energy density and resulting efficiency. For a penetration depth of about 1 and a circular fiber tip having a diameter of about 200μ, this energy is about 150 μJ or greater. For a penetration depth of about 100μ and a circular fiber tip having a diameter of about 200μ, this energy is about 15 mJ or greater. For a penetration depth of about 100μ and a circular fiber tip having a diameter of about 100μ, this energy is about 4 mJ or greater.

With reference to FIGS. 2 and 3, it can be seen that the efficiency curves for 0.5 mJ pulse energy (FIG. 2) and 1 mJ pulse energy (FIG. 3) are very similar, with higher energy being slightly more efficient at the shorter pulse durations. The higher efficiencies are at the shorter pulse durations, but very long pulses (e.g., greater than 20 ns) are still fairly efficient, with efficiencies about 30% (0.3) to 40% (0.4). Efficiency drops very slowly as pulse width increases to substantially larger values.

Contrary to conventional wisdom, pulse durations of 1 ns and above yield high efficiencies. Pulse durations may be used in a range of greater than 1 ns, greater than 1 ns to 100 ns, 2 ns and above, 2 ns to 100 ns, 5 ns and above, 5 ns to 100 ns, 10 ns and above, or 10 ns to 100 ns. Example pulse durations that may be used in accordance with the inventions described herein include at or about 2 ns, at or about 5 ns, at or about 10 ns, at or about 20 ns, as well as other pulse durations greater than 1 ns.

Acceptable pulse duration is roughly proportional to the penetration depth of the laser at the same energy density. For example for a penetration depth of 1 u, a pulse duration of 2 ns, and a pulse energy of 0.5 mJ, an efficiency of 0.45 is predicted. For a 100μ penetration depth, a similar efficiency will be observed at a pulse duration of 200 ns and a pulse energy of 50 mJ.

Persons of ordinary skill in the art reading this disclosure will appreciate that the inventor has invented new and useful ways of operating lasers with advantages over the prior art. The disclosure describes efficient (e.g., efficiency greater than 0.1) infrared lasers for disruptive tissue cutting. Embodiments of the invention have one or more of the following advantages: efficiency of cutting, precision of cutting, no significant heating up of adjacent tissue, and/or no burning of adjacent tissue.

Persons of ordinary skill in the art will appreciate that the embodiments encompassed by the disclosure are not limited to the particular example embodiments described above. While illustrative embodiments have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

Reference 1: Peter Gregorčič, Matija Jezeršek, and Janez Možina, *Optodynamic energy-conversion efficiency during an Er:YAG-laser-pulse delivery into a liquid through different fiber-tip geometries*, Journal of Biomedical Optics 17(7), 075006 (July 2012).

What is claimed is:

1. A method of operating a laser for cataract surgery, comprising:
    operating the laser to emit electromagnetic energy in an infrared range, wherein a wavelength of infrared electromagnetic energy is in a range of 1.8μ to 2.1μ;
    operating the laser in a series of singular pulses, wherein each singular pulse has a pulse duration in a range of 1 ns (nanosecond) to 10 ns;
    wherein the laser electromagnetic energy is delivered from a circular optical fiber tip having a diameter between 100μ to 200μ;

wherein the wavelength and pulse duration of the series of singular pulses are configured to provide photodisruption of a cataract lens;

wherein each singular pulse is configured to be absorbed by water adjacent to the optical fiber tip such that a singular pulse duration is faster than a time it takes for the water absorbing the singular pulse to expand and the water absorbing the singular pulse becomes pressurized and expands into a vapor bubble that pushes adjacent tissue apart to mechanically disrupt the adjacent tissue;

wherein each singular pulse has a pulse energy with an energy density of 2,500 J/cm$^3$ (Joules per cubic centimeters) or greater;

wherein a ratio of energy of the mechanical disruption to a total energy of each singular pulse is between 0.1 and 0.35; and wherein the energy of mechanical disruption equals atmospheric pressure multiplied by a maximum volume of the vapor bubble produced by each singular pulse.

2. The method of operating a laser as recited in claim 1, wherein the pulses have a pulse duration of 2 ns.

3. The method of operating a laser as recited in claim 1, wherein the pulses have a pulse energy selected to deliver an energy density of 10,000 J/cm$^3$ or greater.

4. The method of operating a laser as recited in claim 1, wherein the laser is operated to deliver a pulse energy of 150 µJ or greater.

5. The method of operating a laser as recited in claim 1, wherein the laser is operated to deliver a pulse energy of 4 mJ or greater.

6. The method of operating a laser as recited in claim 1, wherein the pulses have a pulse duration of 5 ns.

7. The method of operating a laser as recited in claim 1, wherein the pulses have a pulse duration of 10 ns.

* * * * *